United States Patent [19]

Barrie et al.

[11] 4,255,656
[45] Mar. 10, 1981

[54] APPARATUS FOR CHARGED PARTICLE SPECTROSCOPY

[75] Inventors: Andrew Barrie; Quentin C. Herd, both of Sale, England

[73] Assignee: Kratos Limited, England

[21] Appl. No.: 42,439

[22] Filed: May 25, 1979

[30] Foreign Application Priority Data

May 25, 1978 [GB] United Kingdom ............... 22583/78

[51] Int. Cl.³ ............................................. H01J 39/00
[52] U.S. Cl. .................................. 250/305; 250/310; 250/423 P; 250/222 R
[58] Field of Search ............... 250/310, 222, 305, 288, 250/423 P

[56] References Cited

U.S. PATENT DOCUMENTS 2,642,537  6/1953  Carroll et al. ...................... 250/272

FOREIGN PATENT DOCUMENTS 1332207 10/1973 United Kingdom ..................... 250/272

Primary Examiner—Harold A. Dixon
Attorney, Agent, or Firm—Leydig, Voit, Osann, Mayer & Holt, Ltd.

[57] ABSTRACT

Charged-particle spectroscopy apparatus for the chemical analysis of a sample in which an apertured plate receives charged particles emitted from the sample and transmits them to an analyzer for analyzing the energies of the particles, the aperture of the plate being such as to restrict the particles passing therethrough to a pencil beam of particles from a selected area of the sample.

4 Claims, 2 Drawing Figures

APPARATUS FOR CHARGED PARTICLE SPECTROSCOPY

BACKGROUND OF THE INVENTION

This invention relates to apparatus for charged-particle spectroscopy.

In British Pat. Specification No. 1,332,207, there is described apparatus for charged-particle spectroscopy for chemical analysis of a sample comprising means for irradiating an extended area of a sample so as to release charged particles from the whole of that extended area, an apertured plate mounted adjacent the sample to receive charged particles from the sample and to transmit said particles, charged-particle focusing means for receiving the transmitted particles and forming a charged particle image in an image plane, and an energy analyser for analysing the energies of the particles passing through the apertured plate.

In the above-mentioned patent specification, charged particles from the whole of the irradiated area of the sample were received by the apertured plate and focussed on to the image plane. Accordingly, difficulty occurred in analysing any selected area forming a small part of the whole irradiated area.

An object of the present invention is to provide apparatus which facilitates analysis and location of a small selected area of the surface of a sample.

BRIEF SUMMARY OF THE INVENTION

According to one aspect of the present invention, there is provided apparatus for charged-particle spectroscopy for chemical analysis of a sample comprising a laser or light directing means for irradiating a selected restricted area of a sample so as to release charged particles from the selected area, by photon excitation, and to visibly identify the irradiated area of the sample, an apertured plate mounted adjacent the sample to receive charged particles therefrom and to transmit a pencil beam of said particles received from the selected restricted area, charged particle focusing means for forming a charged particle image of said selected area in an image plane, and an energy analyser for analysing the energies of the particles passing through the apertured plate.

According to another aspect of the invention, there is provided apparatus for charged-particle spectroscopy for chemical analysis of a sample comprising means for irradiating an extended area of a sample so as to release charged particles from the whole of that extended area, an apertured plate mounted adjacent the sample to receive charged particles therefrom and to transmit a pencil beam of said particles received from a selected restricted part of the extended area, charged particle focusing means for forming a charged particle image of said selected area in an image plane, an energy analyser for analysing the energies of the particles passing through the apertured plate, and a laser, or light-directing means, arranged to direct a beam of radiation through the apertured plate on the axis of said pencil beam to form an illuminated spot on said selected area of the sample thereby providing visual identification of said selected area.

BRIEF DESCRIPTION OF THE DRAWINGS

The invention will now be particularly described with reference to the accompanying drawings in which.

DESCRIPTION OF PREFERRED EMBODIMENTS

Figure 1:
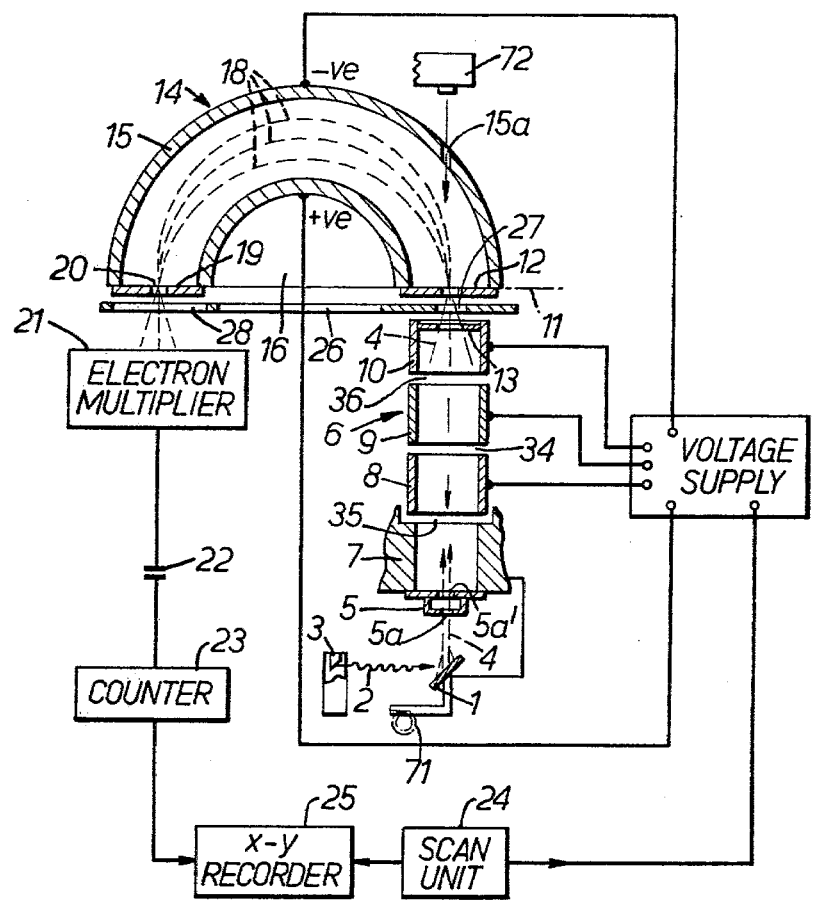
FIG. 1 is a schematic diagram of apparatus for electron spectroscopy for chemical analysis of a specimen.

Referring to FIG. 1, a sample 1 is mounted within a sample chamber (not shown) and is arranged to be irradiated over an extended area by means of a beam 2 of X-rays produced from an X-ray target 3 under electron bombardment or other means. Electrons 4 emitted from the irradiated sample 1 pass through an aperture of a plate 5, held at the same potential as the sample 1, into electron optical focusing means 6 comprising three or more electrostatic lens components 7–10. The components 7–10 are all of uniform internal diameter, (although in modifications they may not be) and are disposed coaxially in line with the aperture of plate 5.

In operation, when suitable potentials are applied to the components 8–10, as described in British Pat. No. 1,332,207, the electrons 4 are focused by the focusing means 6 to form an electron-optical image, in an image plane 11, of the area of the sample forming the source of the electrons passing through the aperture of plate 5. The image may vary in magnification with respect to the sample 1, by a factor greater than unit.

In the above-mentioned patent a source slit was located, in the position occupied in FIG. 1 hereof by apertured plate 5, to receive electrons from a large irradiated area of the sample, and an apertured plate was located in the image plane to allow only some of the electrons, forming the image, to pass. It was therefore necessary to move the apertured plate in the image plane or move the image in order to select the area of the sample to be investigated.

In the present invention, as illustrated, the apertured plate 5 is mounted in a fixed position adjacent the sample. Means 71, shown diagrammatically, are provided for moving the sample relative to the apertured plate 5 in a plane perpendicular to the axis of focussing means 6 in order to locate a selected small area of the sample opposite the aperture 5a of the plate. The plate 5 is provided with an aperture formed by two axially spaced openings 5a, 5a' as shown, or with a single axially elongate opening, to provide an aperture having an inlet and an outlet so spaced apart that only a narrow pencil beam of electrons is allowed to pass through the aperture, thereby restricting the selected area of the sample under investigation.

The image plane 11 coincides with the entry plane of a hemispherical electrostatic analyser 14, comprising a field defining element plate or grid 12 and a pair of metal hemispheres 15, 16, mounted concentrically and mutually electrically insulated. In operation, a voltage is applied between the hemispheres 15, 16, by means of an analyser voltage supply 17, the outer hemisphere 15 being at the negative potential with respect to the inner hemisphere 16. This causes electrons passing through the apertured plate 5 and entering the space between the hemispheres to follow curved trajectories (18 for example) so as to form an electron-optical image of the aperture in the plate 5 in the exit plane 19 of the analyser. It will be appreciated that in fact a large number of images of the aperture are formed in the exit plane 19, since electrons with greater energies will follow trajectories of greater radius of curvature and therefore be focused in different positions.

An exit slit 20 is disposed in the exit plane 19 and serves to select electrons having energies within a certain limited range of the energy spectrum, the electrons so selected being detected by an electron multiplier 21 the output of which produces an output signal proportional to the rate at which electrons arrive through the slit 20.

In operation, the voltage applied from the supply 17 between the hemispheres 15, 16 is swept through a predetermined range of values by means of a scan unit 24, which controls the supply 17, with the result that the exit slit 20 effectively scans through the energy spectrum of the electrons. The output of the counter 23 is fed to the Y-input of an X-Y recorder 25 (for example a strip chart recorder) the X-input being fed from the scan unit 24 by a signal proportional to the electron kinetic energy or the position of the sample drive 71, or slit motor 73. Thus, the recording device produces a record of the energy spectrum of the electrons from the small region of the sample (selected by the apertured plate 5) and thus enables the chemical structure of several small regions on the sample surface to be analysed in a two dimensional sense.

A fringe field plate 26 is situated adjacent the bases of the hemispheres 15, 16 and serves to overcome fringe field effects at the edges of the analyser 14. This plate 26 is of flat annular shape having two apertures 27, 28 respectively adjacent the apertured plate 12 and the exit slit 20, for allowing the passage of electrons into and out of the analyser. The plate 26 is held at a potential intermediate the potentials of the hemispheres 15, 16, by means not shown.

It will be appreciated that all the parts of the apparatus through which the electrons pass must be held in a high vacuum. In addition, there may be provided paramagnetic screening means (not shown), of mu-metal for example, which encloses the analyser 14 and at least a part of the lens system 6 and serves to reduce magnetic and electromagnetic perturbation of the electron trajectories by stray fields.

In order to identify visually the selected area of the sample, a laser or light-directing means 72 is arranged to direct a beam of radiation along the axis of the pencil of electrons passing through apertured plates 12, 11 and 5 in a direction opposite that of the electron flow so that after passing through the apertured plate 5, the radiation forms a visible spot on the selected area of the sample 1. The laser or light source is conveniently located outside the analyser 14, to direct radiation through an aperture 15a in the wall of hemisphere 15.

The laser or light source, instead of being used to visually identify the spot on the sample from which released charged particles are received by the spectrometer, can be used as a source of photon excitation which may be employed to examine the nature of the sample surface, by measuring the ratio of the light absorbed by the surface to the light incident upon the surface, or for example to examine the nature of the sample surface by diffraction techniques.

Figure 2:
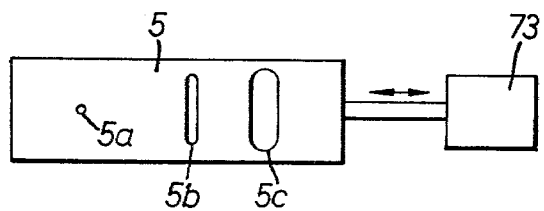
FIG. 2 is a plan view, to an enlarged scale, of part of the apparatus of FIG. 1.

Although plate 5 can be formed only with an aperture or a spaced pair of apertures, as shown in FIG. 1, it is preferable that it be provided also with one or more slits. Such a plate, as shown in FIG. 2, has an aperture 5a, a first narrow slit 5b and a second wider slit 5c. Means 73, such as a positioning motor, are provided for moving the plate 5 longitudinally to located aperture 5a or either of the slits on the axis of the lens 6.

The modes of operation of the apparatus can be as described in British Pat. No. 1,332,207.

What is claimed is:

1. Apparatus for charged-particle spectroscopy for chemical analysis of a sample comprising
   a laser or light directing means for irradiating a selected restricted area of a sample so as to release charged particles from the selected area by photon excitation, and to visibly identify the irradiated area of the sample,
   an apertured plate mounted adjacent the sample to receive charged particles therefrom and to transmit a pencil beam of said particles received from the selected restricted area,
   charged particle focusing means for forming a charged particle image of said selected area in an image plane, and
   an energy analyser for analysing the energies of the particles passing through the apertured plate.

2. Apparatus for charged-particle spectroscopy for chemical analysis of a sample comprising
   means for irradiating an extended area of a sample so as to release charged particles from the whole of that extended area,
   an apertured plate mounted adjacent the sample to receive charged particles therefrom and to transmit a pencil beam of said particles received from a selected restricted part of that extended area,
   charged particle focusing means for forming a charged particle image of said selected area in an image plane,
   an energy analyser for analysing the energies of the particles passing through the apertured plate, and a laser, or light-directing means, arranged to direct a beam of radiation through the apertured plate on the axis of said pencil beam to form an illuminated spot on said selected area of the sample thereby providing a visual identification of said selected area.

3. Apparatus according to claim 1 or claim 2 wherein the analyser has an internally-convex wall containing an aperture and said laser or light-directing means is located opposite said aperture.

4. Apparatus according to claim 1, or claim 2 wherein said laser, or light-directing means, is arranged to direct a beam of radiation through the apertured plate on the axis of said pencil beam to impinge on the sample.

* * * * *